United States Patent
Okada et al.

(10) Patent No.: US 6,992,781 B2
(45) Date of Patent: Jan. 31, 2006

(54) FILM THICKNESS MEASURING METHOD AND MEASURING APPARATUS FOR ORGANIC THIN FILM FOR USE IN ORGANIC ELECTROLUMINESCE DEVICE

(75) Inventors: Hiroyuki Okada, Toyama (JP); Miki Shibata, Takaoka (JP); Tadahiro Echigo, Uozu (JP); Shigeki Naka, Nei-gun (JP); Hiroyoshi Onnagawa, Toyama (JP)

(73) Assignee: President of Toyama University, Toyama (JP)

( * ) Notice: Subject to any disclaimer, the term of this patent is extended or adjusted under 35 U.S.C. 154(b) by 194 days.

(21) Appl. No.: 10/389,751

(22) Filed: Mar. 18, 2003

(65) Prior Publication Data

US 2003/0193672 A1    Oct. 16, 2003

(30) Foreign Application Priority Data

Mar. 26, 2002 (JP) ............................. 2002-086992

(51) Int. Cl.
H01L 27/15 (2006.01)
G01B 11/28 (2006.01)

(52) U.S. Cl. .................................. 356/630; 250/459.1
(58) Field of Classification Search ................ 356/630, 356/128, 73; 250/459.1, 461.1, 372, 559.27, 250/559.34, 559.45; 427/492
See application file for complete search history.

(56) References Cited

U.S. PATENT DOCUMENTS 4,292,341 A    9/1981  Marcuse et al.
4,841,156 A *  6/1989  May et al. ............... 250/461.1
5,001,353 A    3/1991  Odake et al.
5,281,819 A    1/1994  Keffert et al.
5,414,506 A *  5/1995  Saisho et al. ............... 356/128
5,604,581 A *  2/1997  Liu et al. ...................... 356/73
5,844,249 A * 12/1998  Takano et al. ........... 356/237.1
5,986,268 A * 11/1999  Forrest et al. .............. 250/372

(Continued)

FOREIGN PATENT DOCUMENTS

EP          0 336 029         10/1989

(Continued)

OTHER PUBLICATIONS

C.W. Tang, et al. "Organic Electroluminescent Diodes" Appl. Phys. Lett. 51 (12), Sep. 21, 1987, pp. 913-915.

Primary Examiner—Gregory J. Toatley, Jr.
Assistant Examiner—Sang H. Nguyen
(74) Attorney, Agent, or Firm—Oblon, Spivak, McClelland, Maier & Neustadt, P.C.

(57) ABSTRACT

A method for measuring a relative thickness distribution of an organic thin film for use in an organic electroluminescence device comprises the steps of irradiating a predetermined region of the organic thin film with a light including an ultraviolet light, measuring the intensity of a fluorescence produced by the organic thin film in response to the light irradiation, and obtaining a film thickness of the predetermined region from the intensity of the fluorescence. Further, an apparatus for measuring a thickness distribution for use in an organic electroluminescence device has means for irradiating a predetermined region of the organic thin film with a light including an ultraviolet light, means for measuring the intensity of a fluorescence produced by the organic thin film, and means for obtaining the film thickness of the predetermined region from the intensity of the fluorescence.

21 Claims, 6 Drawing Sheets

U.S. PATENT DOCUMENTS

| | | | |
|---|---|---|---|
| 6,025,036 A * | 2/2000 | McGill et al. | 427/492 |
| 6,252,237 B1 * | 6/2001 | Ramthun et al. | 250/459.1 |
| 6,529,273 B1 * | 3/2003 | Norris et al. | 356/630 |
| 6,594,025 B2 * | 7/2003 | Forouhi et al. | 356/630 |
| 2001/0046045 A1 | 11/2001 | Dong et al. | |

FOREIGN PATENT DOCUMENTS

| | | |
|---|---|---|
| EP | 1 180 660 | 2/2002 |
| JP | 3-252512 | 11/1991 |
| JP | 2000-294372 | 10/2000 |

* cited by examiner

US 6,992,781 B2

FILM THICKNESS MEASURING METHOD AND MEASURING APPARATUS FOR ORGANIC THIN FILM FOR USE IN ORGANIC ELECTROLUMINESCE DEVICE

CROSS-REFERENCE TO RELATED APPLICATIONS

This application is based upon and claims the benefit of priority from the prior Japanese Patent Application No. 2002-086992, filed Mar. 26, 2002, the entire contents of which are incorporated herein by reference.

BACKGROUND OF THE INVENTION

1. Field of the Invention

The present invention relates to a film thickness measuring method and a film thickness measuring apparatus using fluorescence which is applicable to measurement of the film thickness of an organic electroluminescence device (hereinafter referred to as an organic EL device).

2. Description of the Related Art

Organic EL devices are rapidly coming into practical use, after an organic light emitting device having characteristics such as high luminance, low voltage drive, small size and high efficiency was published in Applied Physics Letters [51(12), pp. 913 to 915 (1987)] in 1987 by C. W. Tang and S. A. VanSlyke. Tang et al. formed an ultra-thin film of an organic dye, thereby increasing the efficiency of the conventional organic light-emitting device by a factor of 10. Note that the organic dye they used can easily be processed into an amorphous film. According to this report, an external quantum efficiency of 1%, a visual luminous efficiency of 1.5 lm/W and a luminance of 1000 $cd/m^2$ are achieved with a driving voltage of 10 V or less. Furthermore, the reduction of voltage is achieved by using a magnesium silver alloy having a relatively small work function as a cathode. Ten years have passed since the above report, and present organic EL deices have a higher efficiency and longer life, and matrix panels are also commercially available.

The organic EL device has such characteristics as spontaneous luminance, thinness, low weight, high luminance and high efficiency, and is expected as a next-generation flat-panel display. The basic configuration of an organic EL device is shown in FIG. 1. In the organic EL device of FIG. 1, a transparent electrode 2 made of an electrode material transparent in a visible region such as ITO (Indium Tin Oxide) is formed on a transparent substrate 1 such as glass, quartz or a plastic film. This transparent electrode 2 has a thickness of about 100 nm, for example. On the surface of the transparent electrode 2, there are deposited a hole transport thin film 3 of about 50 nm made of a hole transport thin film material, and an electron transport light emitting thin film 4 of about 50 nm made of an electron transport light emitting thin film material. In addition, an upper electrode 5 having a thickness of about 50 nm to 200 nm is formed on the surface of the electron transport light emitting thin film 4. The organic EL device of FIG. 1 has a double layer structure, but recently, devices having multi layer structures, such as a three or four layer structure have also been developed.

As shown in FIG. 1, the organic EL device has permeability in at least one of the electrodes in the visible region, and has a configuration having an ultra thin organic film of about 100 nm (e.g., 3 and 4 of FIG. 1) between the electrodes 2 and 5 of the device. Its driving voltage characteristics largely depend upon the thickness of the organic thin film, meaning that obtaining uniformity in thickness of the organic thin film within the surface has been a significant challenge. This is because nonuniformity of the film thickness caused during formation of the organic thin film could lead to a reduced yield. If a film thickness distribution can be measured, especially during film formation, and is fed back to a film forming apparatus, improvements in the uniformity of the film within the surface, will result, and the yield will be raised, reducing costs.

To date various methods and apparatuses have been used to measure the thickness during formation or after formation of an organic thin film in an organic EL device. For example, in the organic EL device of FIG. 1, the thickness may need to be measured during formation or after formation of the hole transport thin film 3, and during formation or after formation of the electron transport light emitting thin film 4 thereon. Regarding the principal methods of measuring the film thickness, a quartz oscillator method is widely used during film formation in vacuum, and a film thickness measuring method using light interference in the film after formed, as they utilize nondestructive and non-contact methods. Further, when a film is formed by screen printing, spraying or application, the film thickness is normally measured by use of, for example, light interference after film formation.

To put it simply, the principle of measurement in accordance with the quartz oscillator method is that the natural oscillation of the quartz oscillator changes along with its mass change. In other words, it utilizes the fact that when a thin film is deposited on the quartz oscillator, the same effects are simply produced as those of increased mass or thickness of the quartz oscillator if the mass of the thin film is sufficiently lower than the mass of the quartz oscillator, thus producing a natural oscillation frequency change proportionate to the mass change.

In the film thickness measuring method using light interference, when the film is irradiated with a constant wavelength light, luminous flux which has permeated through the film, has been reflected on the bottom surface and returned up to the surface and luminous flux reflected on the film surface cause interference. By measuring prisms that have caused the interference and analyzing upper and lower peak positions of the interference, the film thickness can be obtained.

However, the above quartz oscillator method is a method in which the thickness of the organic thin film on the transparent substrate is not directly observed, and the film thickness is estimated from deposits accumulated on the quartz oscillator set in the same vacuum device. It is thus essentially impossible to directly measure the thickness of the organic thin film formed on the transparent substrate. Therefore, it is impossible to measure the film thickness distribution of the organic thin film formed for use in, for example, flat panel displays, in a nondestructive manner during a production process. Further, such a disadvantage is caused that, when used simply to monitor the film thickness during a production process, the quartz oscillator must be replaced, if the natural oscillation frequency of the quartz oscillator is significantly decreased due to accumulated deposits.

On the other hand, when the film thickness measuring method using light interference is used, the film thickness distribution of the organic thin film on the substrate can be nondestructively measured, but the problem is that this is extremely complicated.

BRIEF SUMMARY OF THE INVENTION

The present invention overcomes the problems described above, and its object is to provide, in the thickness measurement of an organic thin film for use in an organic EL device, a film thickness measuring method which enables thickness measurement of the organic thin film by use of a method in which the organic thin film is irradiated with light and the intensity of a fluorescence emitted by the organic thin film is measured.

According to an embodiment of the present invention, a method for measuring a relative thickness distribution of an organic thin film for use in an organic EL device comprises the steps of: irradiating a predetermined region of the organic thin film with a light including an ultraviolet light; measuring the intensity of a fluorescence produced by the organic thin film in response to the light irradiation; obtaining a film thickness of the predetermined region of the organic thin film from the intensity of the fluorescence; and obtaining the film thickness distribution of the organic thin film from the film thickness of each region of the organic thin film. Further, the above measuring method comprises the steps of: placing the organic thin film on an XY movable stage; and scanning light irradiated positions in the organic thin film by the XY movable stage.

According to another embodiment of the present invention, a method for measuring a relative thickness distribution of an organic thin film for use in an organic EL device comprises the steps of: irradiating the organic thin film with a light including an ultraviolet light; measuring, by a two-dimensional sensor, the intensity of a fluorescence produced by each portion of a measurement region of the organic thin film in response to the light irradiation; obtaining the film thickness of each portion of the organic thin film from the measured intensity of the fluorescence; and obtaining the film thickness distribution of the organic thin film from the film thickness of each portion of the organic thin film. In the measuring method, the two-dimensional sensor is a two-dimensional CCD sensor.

Furthermore, a method for forming an organic thin film by a vacuum deposition method comprises the step of: measuring a film thickness by any of the above measuring methods to control the thickness of the organic thin film. Alternatively, a method for forming an organic thin film by a spin coat method comprises the step of: measuring a film thickness by any of the above measuring methods to control the thickness of the organic thin film. Alternatively, a method for forming an organic thin film by a spray coat method comprises the step of: measuring a film thickness by any of the above measuring methods to control the thickness of the organic thin film.

According to a further embodiment of the present invention, an apparatus for measuring a relative thickness distribution of an organic thin film for use in an organic EL device has: means for irradiating a predetermined region of the organic thin film with a light including an ultraviolet light; means for measuring the intensity of a fluorescence produced by the organic thin film; and means for obtaining the film thickness of the predetermined region from the intensity of the fluorescence; wherein the film thickness distribution of the organic thin film is obtained from the thickness of each region of the organic thin film. Further, the above measuring apparatus further has an XY movable stage for mounting the organic thin film thereon, and enabling light irradiated positions in the organic thin film to be scanned.

According to another embodiment of the present invention, an apparatus for measuring a relative thickness distribution of an organic thin film for use in an organic EL device has: means for irradiating a measurement region of the organic thin film with a light including an ultraviolet light; means for measuring the intensity of each fluorescence produced by each portion of the organic thin film; and means for obtaining the film thickness of each portion of the measurement region from the intensity of each fluorescence; wherein the film thickness distribution of the organic thin film is obtained from the film thickness of each portion of the organic thin film. Further, in the film thickness measuring apparatus, the means for measuring the intensity of each fluorescence is a two-dimensional CCD sensor.

Furthermore, in an apparatus for forming an organic thin film by a vacuum deposition method, a film thickness is controlled by a thickness control device for the organic thin film connected to any of the above measuring apparatuses, and in an apparatus for forming an organic thin film by a spin coat method, a film thickness is controlled by a thickness control device for the organic thin film connected to any of the above measuring apparatuses, and yet in an apparatus for forming an organic thin film by a spray coat method, a film thickness is controlled by a thickness control device for the organic thin film connected to any of the above measuring apparatuses.

DETAILED DESCRIPTION OF THE INVENTION

Figure 1:
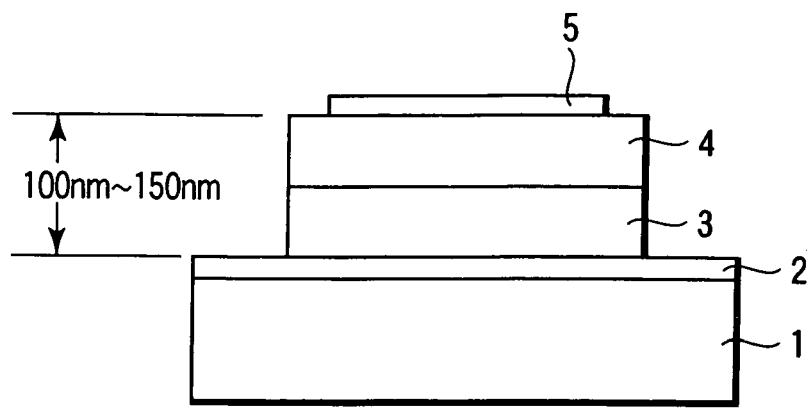
FIG. 1 is a diagram showing a cross section configuration of an organic EL device.

The present invention will hereinafter be described in detail in accordance with specific embodiments shown in the accompanying drawings. In the description of the embodiments below and the illustration in the drawings, like reference numerals indicate like elements.

Figure 2:
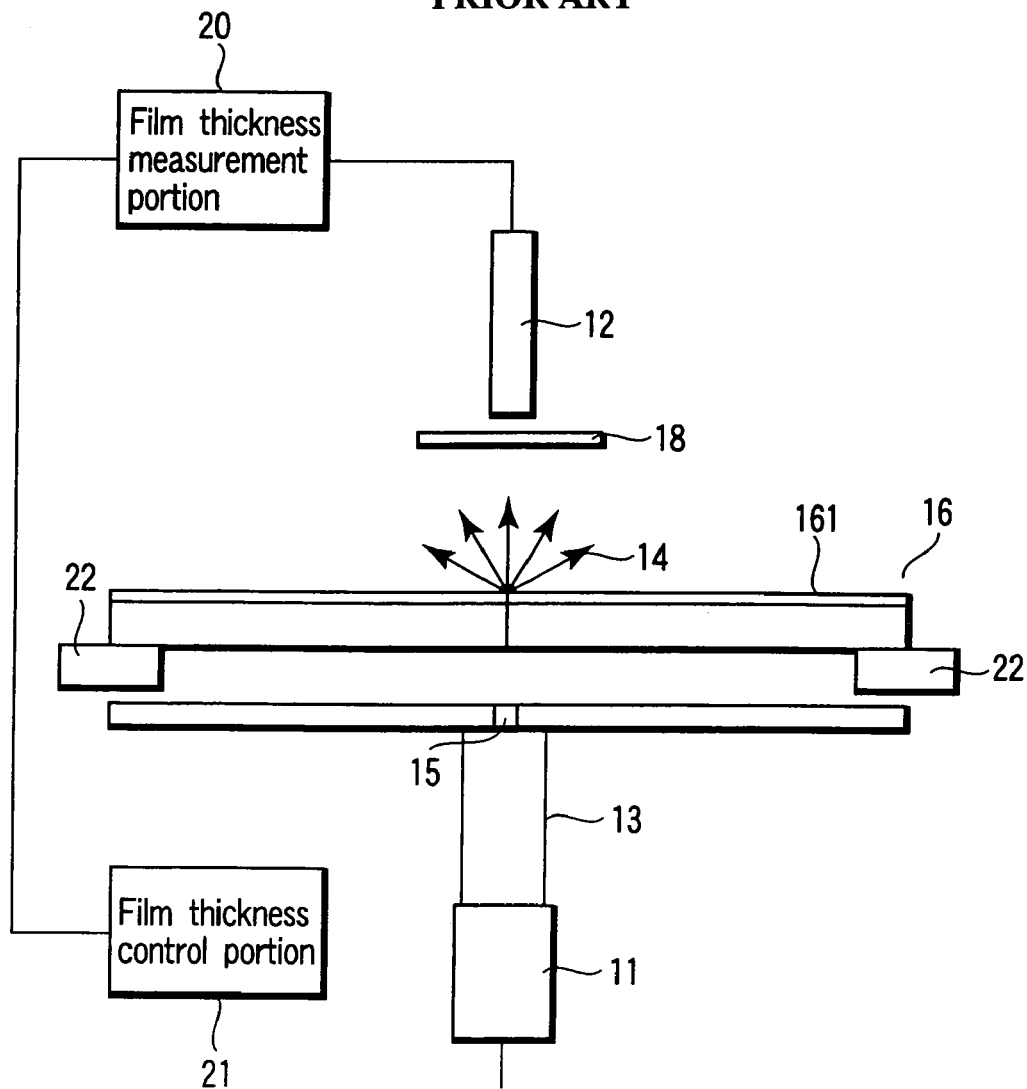
FIG. 2 is a conceptual diagram of a fluorescence film thickness measuring apparatus in a first embodiment of this invention.

FIG. 2 shows a first embodiment of this invention, and there are provided a pin hole 15 disposed between an ultraviolet light source 11 disposed under an organic EL device 16 and the organic EL device 16, and a photodetector 12 disposed above the organic EL device 16. The pin hole 15 may be disposed between the organic EL device 16 and the photodetector 12. An ultraviolet light protection filter 18 may be provided between the organic EL device 16 and the photodetector 12 as needed.

As the ultraviolet light source 11, it is possible to use a light source capable of releasing an ultraviolet light, such as a fluorescent test light, xenon lamp, deuterium lamp or nitrogen laser, having a wavelength to excite organic materials constituting the organic EL device 16, preferably a wavelength of 200 nm to 380 nm. For the photodetector 12, a photodiode, a phototransistor, a multichannel spectroscope and a CCD sensor are available, for example. By disposing the organic EL device on an XY movable stage 22, it is possible to readily measure a film thickness distribution within a surface. For example, an interference filter having a plurality of transparent dielectric thin film layers with different refractive indices optical thickness of which is on a level of the wavelength can be used for the ultraviolet light protection filter 18. In this case, it is possible to use a long wavelength pass light filter for shutting off the irradiated ultraviolet light, or a band pass light filter for mainly allowing only excitation light inherent in each organic material to pass.

An organic thin film 161 is irradiated with an ultraviolet light 13 emitted from the ultraviolet light source 11 through the pin hole 15. The size of the pin hole 15 is determined in accordance with each evaluation region of the film thickness, and the diameter of which is desirably about 10 $\mu$m to 1000 $\mu$m, for example. The organic thin film 161 thereby produces a fluorescence 14 inherent in the organic material, and the intensity of the fluorescence is detected by the photodetector 12. For example, the relationship between the fluorescence intensity and the film thickness is previously obtained by way of experiment, and the fluorescence intensity, which has been measured in a film thickness measurement portion 20, such as a digital multimeter, having a memory (not shown) for storing the relationship, is converted into a film thickness, thereby obtaining the film thickness for each evaluation region. Further, the film thickness measurement portion 20 can also be constituted to have a CPU (not shown) for corresponding the measured film thickness with each scanning position based on the XY movable stage, so as to derive an in-surface distribution of the thickness of the organic material thin film. Especially in the first embodiment, the ultraviolet light 13 is applied vertically from a lower side to the organic thin film 161, as shown in FIG. 2, so that the irradiation area can be accurately limited in the direction of the thin film thickness, thereby enabling highly accurate film thickness measurement.

Generally, the organic EL device is laminated with a plurality of different organic thin films. In this case, it is possible to obtain the thickness separately for each organic thin film by applying waveform separation to a fluorescence spectrum of each organic thin film and obtaining a spectrum intensity corresponding to each of a plurality of laminated films. In addition, when, for example, the film thickness of the organic EL device shown in FIG. 1 is to be evaluated, a plurality of filters are respectively provided which have such a permeation band that allows only the inherent fluorescence emitted by each of thin film layers 3 and 4 to pass, and these filters are sequentially interchanged and used, thereby enabling the thickness of the plurality of thin film layers 3 and 4 to be separately measured.

An example of measurement in the first embodiment will be described below. In this case, the thin film layer to be evaluated has one layer. A mixture of polyvinylcarbazole and a coumarin pigment is applied onto a glass substrate on which a film of indium tin oxide (hereinafter referred to as ITO) is formed by a spray method usually used for film formation, from a dichloroethane solution in which polyvinylcarbazole and the coumarin dye are mixed. It should be noted that, for forming a thin film for use in the general organic EL devices including the above organic material mixture, it is possible to apply a vacuum deposition method or a spin coat method known to those skilled in the art as a normal film formation method, in addition to the above spray coat method, depending upon the kind of organic material.

Figure 10:
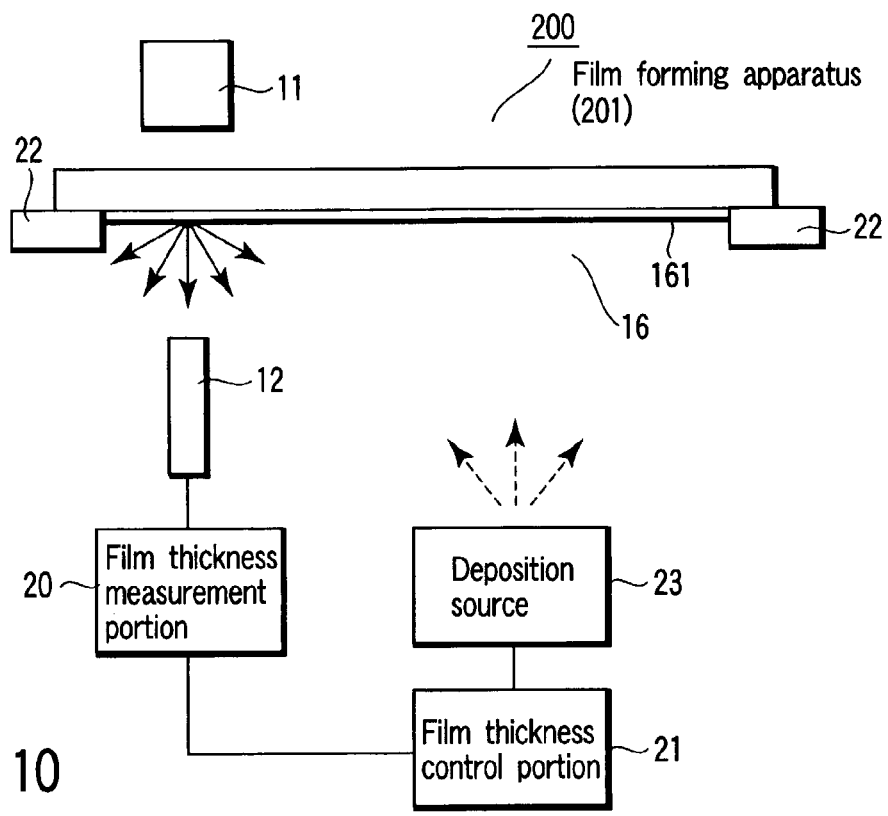
FIG. 10 is a film forming apparatus of this invention.
Figure 11:
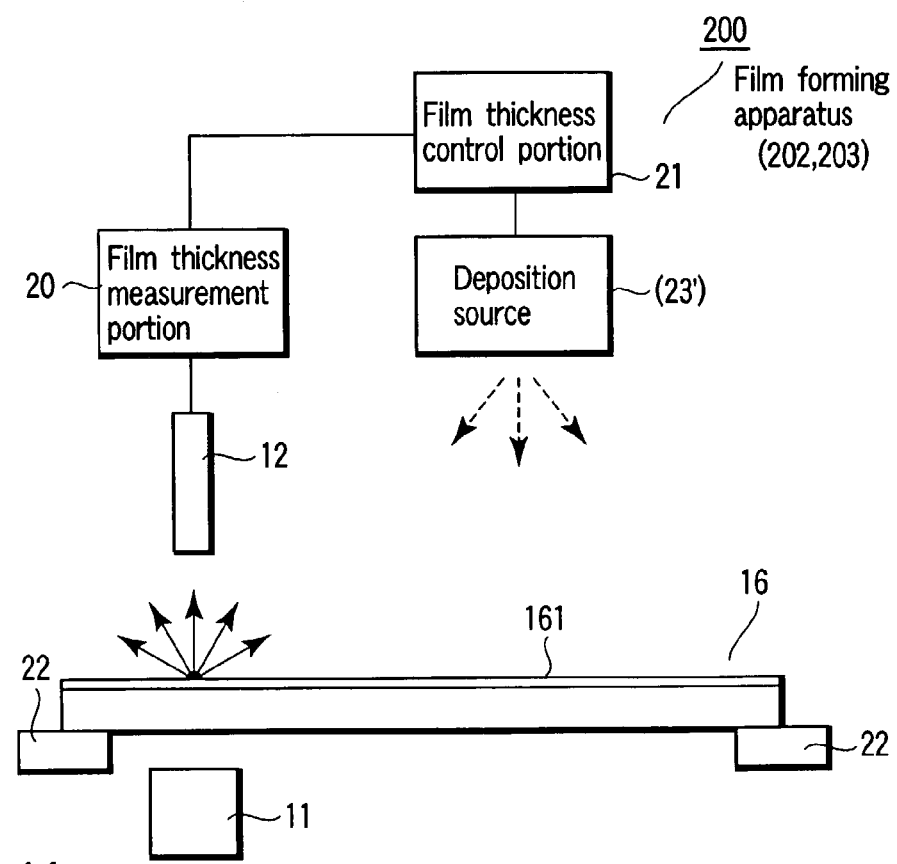
FIG. 11 is a film forming apparatus of this invention.

Therefore, it is possible to use a vacuum deposition apparatus 201, spin coat apparatus 202 or spray coat apparatus 203, as a film forming apparatus 200, in conformity with the properties of the organic material for film formation (e.g., refer to FIGS. 10, 11). The spin coat method is a method in which, for example, while the transparent substrate is rotated, an organic material in a liquid form to be formed into a film is dropped onto the surface of the transparent substrate, thereby forming an organic thin film having a desired thickness. The spray method is a method in which, for example, an organic material in a liquid form to be formed into a film is loaded into an injection portion 23' of a spray apparatus, and the organic material is sprayed onto the surface of the transparent substrate so as to form an organic thin film having a desired thickness. The thickness of a coating film by the simple spray method used in this embodiment is supposedly thicker directly under the spray, and this with distance therefrom.

ITO does not produce fluorescence by the irradiation of ultraviolet light, and a green fluorescence derived from the coumarin dye is observed by irradiating the coating film of the mixture of polyvinylcarbazole and the coumarin dye with ultraviolet rays.

A fluorescent test light (FI-3L manufactured by Toshiba Corporation) is placed as the light source 11 under the organic EL device 16, and a fiber multichannel spectroscope (S2000 manufactured by Ocean Optics Corporation) is placed as the photodetector 12 above the organic EL device 16. The intensity of the fluorescence and fluorescence spectrum measured by the fiber multichannel spectroscope are displayed, for example, chronologically on a screen of a personal computer (not shown) constituting the measurement portion 20, and can be stored in its storage portion. In addition, the pin hole 15 and the ultraviolet light protection filter 18 are placed between the back light 11, which is the light source, and the multichannel spectroscope 12.

Figure 7:
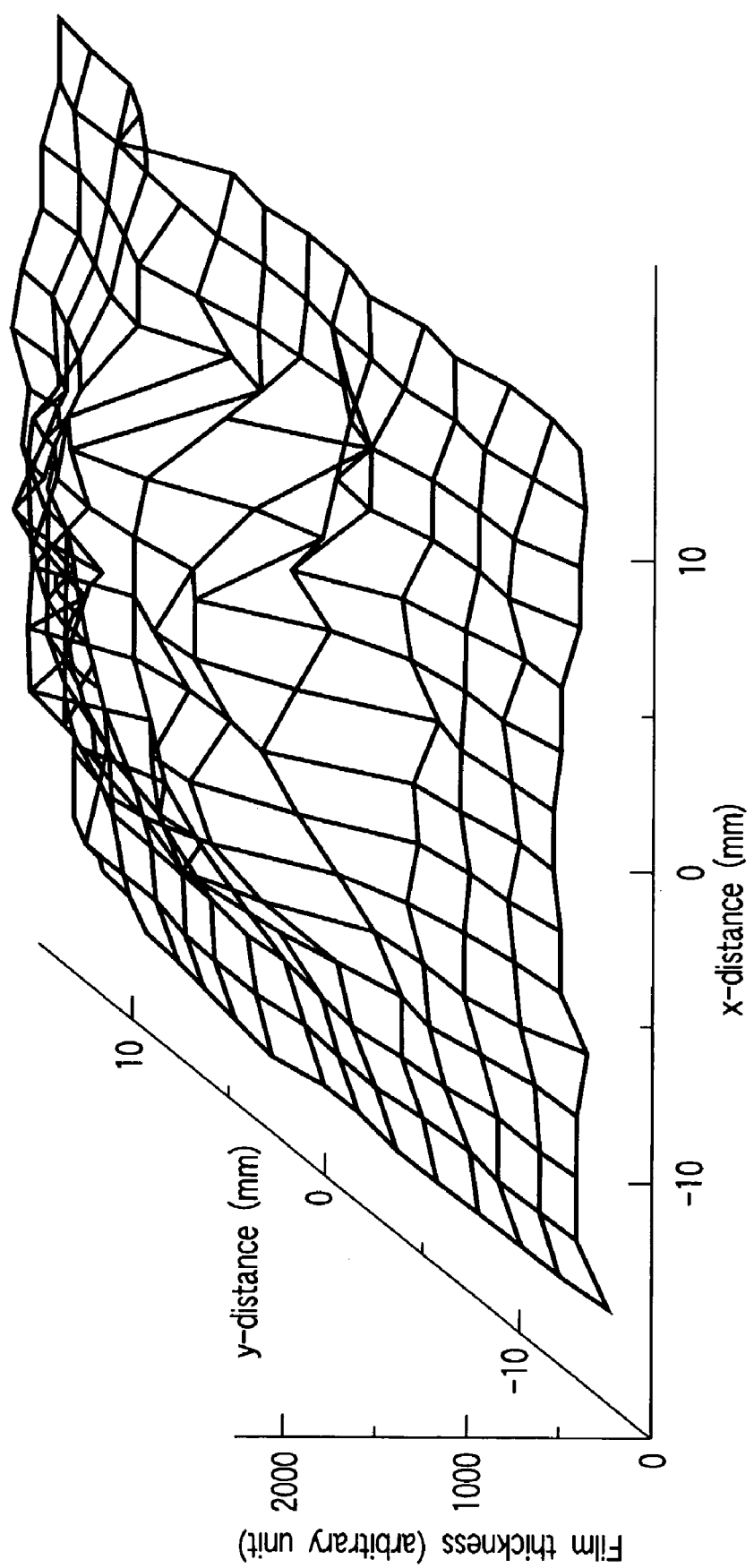
FIG. 7 is a diagram showing the measurement results of an in-surface distribution of film thickness according to the first embodiment.

The transparent substrate on which the organic thin film is formed is placed on the XY movable stage, and the in-surface distribution of the fluorescence intensity is measured every 2 mm. From the relationship between the fluorescence intensity and the film thickness previously obtained, the in-surface distribution of the thickness of the organic material thin film can be measured. The measured thickness in-surface distribution of the coating film made of the mixture of polyvinylcarbazole and the coumarin dye is shown FIG. 7. The vertical axis indicates the film thickness in arbitrary units. Since the organic material thin film is made by coating in accordance with the spray method in this embodiment, such a state is shown that the film thickness is thicker directly under the spray at a central portion and becomes thinner as the distance increases from the position directly under the spray.

Furthermore, when the organic thin film is produced by deposition, by placing a measurement system shown in FIG. 2 in the vacuum deposition apparatus 201 and measuring the fluorescence intensity of the organic thin film at the same time as the organic thin film deposition, the film thickness can be controlled by a film thickness control portion 21 such as a personal computer. The film thickness control portion 21 transmits a control signal, on the basis of the time-related change of the film thickness, to a power source (not shown) of a deposition source 23 and a shutter controller (not shown), which is normally used with the deposition source, for controlling the passing amount of the organic thin film material, thereby allowing the deposition rate and completion of the deposition at a target film thickness to be controlled. In this case, the film thickness can be controlled by measuring the film thickness at one place or a plurality of places previously designated. Alternatively, the film thickness distribution is measured on the entire organic thin film as required, and film formation conditions are evaluated on the basis of the measurement results, whereby the film thickness can also be controlled.

Figure 3:
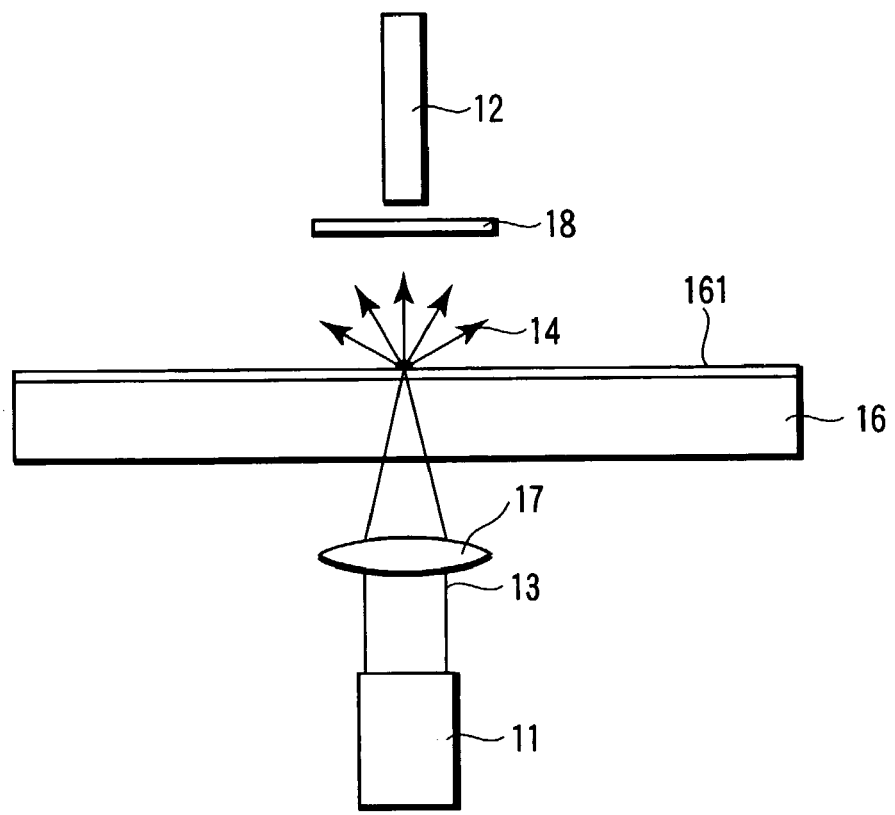
FIG. 3 is a conceptual diagram of the fluorescence film thickness measuring apparatus in a second embodiment of this invention.

FIG. 3 shows a second embodiment of this invention, and there are provided a lens system 17 disposed between the ultraviolet light source 11 disposed under the organic EL device 16 and the organic EL device 16, and the photodetector 12 disposed above the organic EL device 16. The ultraviolet light protection filter 18 may be provided between the organic EL device 16 and the photodetector 12 as needed. It should be noted that the film thickness measurement portion 20 and the film thickness control portion 21 are not illustrated in FIG. 3 to FIG. 6.

As the ultraviolet light source 11, it is possible to use a fluorescent test light, xenon lamp, deuterium lamp or nitrogen laser, having a wavelength which excites the organic material 161 constituting the organic EL device 16, preferably a wavelength of 200 nm to 380 nm. For the photodetector 12, a photodiode, phototransistor and multichannel spectroscope are available, for example.

By disposing the organic EL device 16 on the XY movable stage 22, it is possible to readily measure the film thickness distribution within the surface. The organic thin film 161 is irradiated with the ultraviolet light 13 emitted from the ultraviolet light source 11 through the lens system 17. FIG. 3 shows the case where one lens is used, but a lens system combining a plurality of lenses can be used as necessary.

By condensing the ultraviolet light 13 using the lens system 17, it is possible to excite in a narrower range, so that the resolution within the surface during the film thickness distribution measurement will be improved. The organic thin film 161 produces the fluorescence 14 inherent in the organic material in a minute area, owing to the condensed ultraviolet light irradiation, and the photodetector 12 detects the fluorescence intensity in this area. The diameter of the condensing portion is desirably about 10 $\mu$m to 1000 $\mu$m, for example. Generally, the organic EL device is often laminated with, for example, three or four layers of different organic thin films. In this case, it is possible to separately obtain the film thickness in the minute area of the organic thin films made of different materials by applying waveform separation to the fluorescence spectrum of each organic thin film by a general spectrum waveform separating means, or by sequentially and separately obtaining the peak spectrum intensity corresponding to each organic film.

Furthermore, when the organic thin film is produced by deposition, as in the first embodiment, by placing the measurement system in the vacuum apparatus and measuring the fluorescence intensity of the organic thin film as described above, the deposition rate and the film thickness can be controlled.

Figure 4:
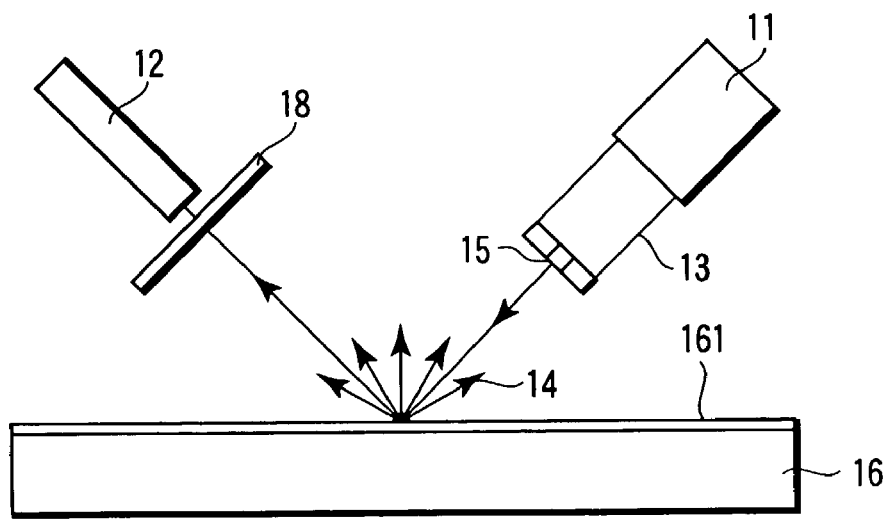
FIG. 4 is a conceptual diagram of the fluorescence film thickness measuring apparatus in a third embodiment of this invention.

FIG. 4 shows a third embodiment of this invention, and there are provided the pin hole 15 disposed between the ultraviolet light source 11 disposed above the organic EL device 16 and the organic EL device 16, and the photodetector 12 disposed above the organic EL device 16. The pin hole 15 is set between the ultraviolet light source 11 and the organic EL device 16 in the embodiment shown in FIG. 4, but instead of this, the pin hole 15 may be disposed between the organic EL device 16 and the photodetector 12. The ultraviolet light protection filter 18 may be provided between the organic EL device 16 and the photodetector 2 as needed.

As the ultraviolet light source 11, it is possible to use a fluorescent test light, xenon lamp, deuterium lamp or nitrogen laser, having a wavelength to excite the organic materials constituting the organic EL device 16, preferably a wavelength of 200 nm to 380 nm, as in the first embodiment. For the photodetector 12, the photodiode, phototransistor and multichannel spectroscope are available, for example. By disposing the organic EL device on the XY movable stage 22, it is possible to readily measure the film thickness distribution within the surface. As compared with the first and second embodiments, it is possible to eliminate the influence of the transparent substrate (e.g., refer to 1 of FIG. 1) on which the organic thin film 161 is directly disposed and the influence of the transparent electrode (e.g., refer to 2 of FIG. 1) disposed between the transparent substrate and the organic thin film 161, since the organic thin film 161 is directly irradiated with the ultraviolet light from above the organic EL device 16.

The organic thin film 161 is irradiated with the ultraviolet light 13 emitted from the ultraviolet light source 11 through the pin hole 15. The organic thin film 161 thus produces the fluorescence 14 inherent in the organic material, and the photodetector 12 detects its fluorescence intensity. Generally, the organic EL device is often laminated with different organic thin films. In this case, it is possible to separately obtain the thickness of each organic thin film by applying waveform separation to the fluorescence spectrum of each organic thin film by proper spectrum separating means and obtaining the spectrum intensity of each film.

Furthermore, when the organic thin film is produced by deposition, as in the first embodiment, by placing the measurement system in the vacuum apparatus and measuring the fluorescence intensity of the organic thin film at the same time as the organic thin film deposition, the film thickness can be controlled. The time-related change of this fluorescence intensity or the film thickness is fed back to the power source (not shown) of the deposition source and the shutter controller, which is normally used with the deposition source, for controlling the passing amount of the organic thin film material, thereby allowing the deposition rate and completion of the deposition at a target film thickness to be controlled.

Figure 5:
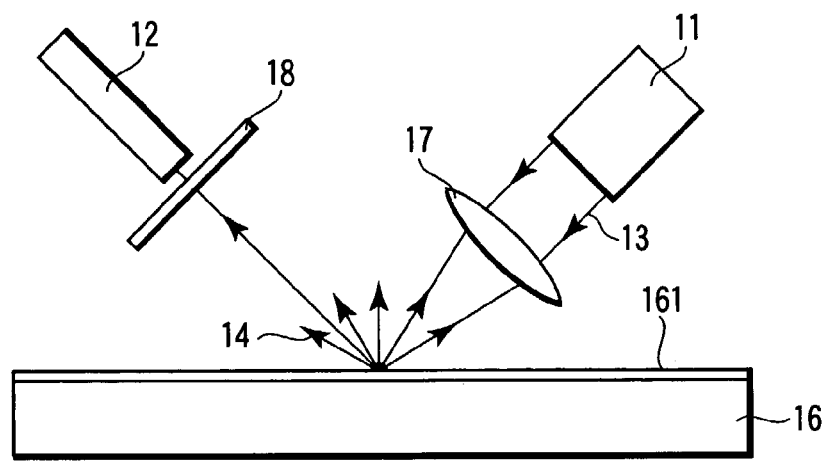
FIG. 5 is a conceptual diagram of the fluorescence film thickness measuring apparatus in a fourth embodiment of this invention.

FIG. 5 shows a fourth embodiment of this invention, and there are provided a lens 17 disposed between the ultraviolet light source 11 disposed above the organic EL device 16 and the organic EL device 16, and the photodetector 12 disposed above the organic EL device 16. The ultraviolet light protection filter 18 may be provided between the organic EL device 16 and the photodetector 12 as needed.

As the ultraviolet light source 11, it is possible to use a fluorescent test light, xenon lamp, deuterium lamp or nitrogen laser, having a wavelength to excite the organic materials constituting the organic EL device 16, preferably a wavelength of 200 nm to 380 nm, as shown in the embodiments described above. Also, for the photodetector 12, the photodiode, phototransistor and multichannel spectroscope are available, for example. By disposing the organic EL device 16 on the XY movable stage, it is possible to readily measure the film thickness distribution within the surface.

The organic thin film 161 is irradiated with the ultraviolet light 13 emitted from the ultraviolet light source 11 through the lens 17. By condensing the ultraviolet light with the lens 17, it is possible to excite in a narrower range, so that the resolution within the surface during the film thickness distribution measurement will be improved. The organic thin film 161 thus produces the fluorescence 14 inherent in the organic material, and the photodetector 12 detects its fluorescence intensity. Generally, the organic EL device is often laminated with different organic thin films. In this case, it is possible to separately obtain the thickness of each organic thin film by applying waveform separation to the fluorescence spectrum of each organic thin film and obtaining the spectrum intensity of each film.

Furthermore, as in the third embodiment, by placing these in the vacuum apparatus and measuring the fluorescence intensity of the organic thin film at the same time as the organic thin film deposition, the film thickness can be controlled. The time-related change of this fluorescence intensity or the measured film thickness is fed back to the power source of the deposition source and the shutter controller, thereby allowing the deposition rate and completion of the deposition at a target film thickness to be controlled.

Figure 6:
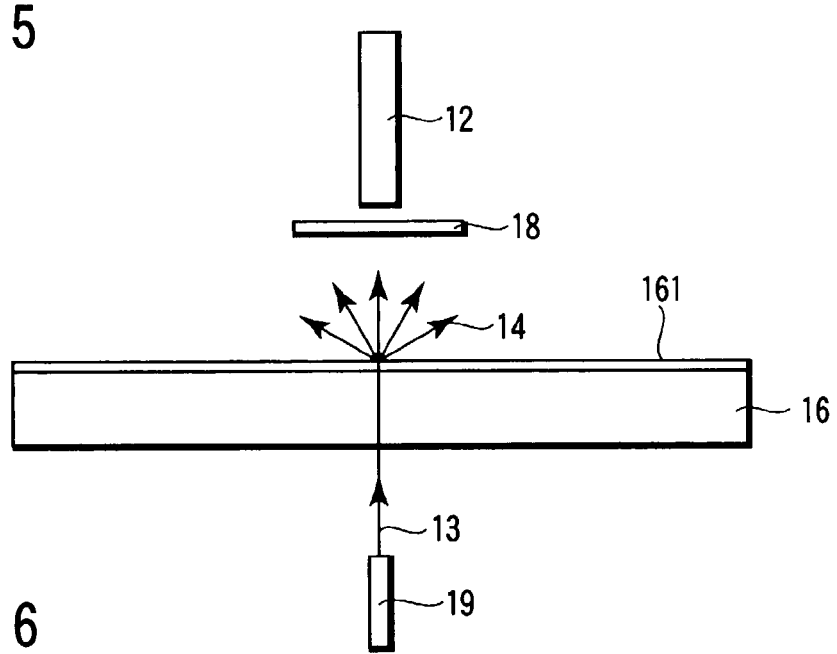
FIG. 6 is a conceptual diagram of the fluorescence film thickness measuring apparatus in a fifth embodiment of this invention.

FIG. 6 shows a fifth embodiment of this invention. Such a case is shown that, instead of the pin hole 15 in the first embodiment shown in FIG. 2, or the les system in the second embodiment shown in FIG. 3, an optical fiber 19 is used to apply the ultraviolet light. In this case, it is preferable to use the ultraviolet light such as laser light that moves straight.

Figure 8:
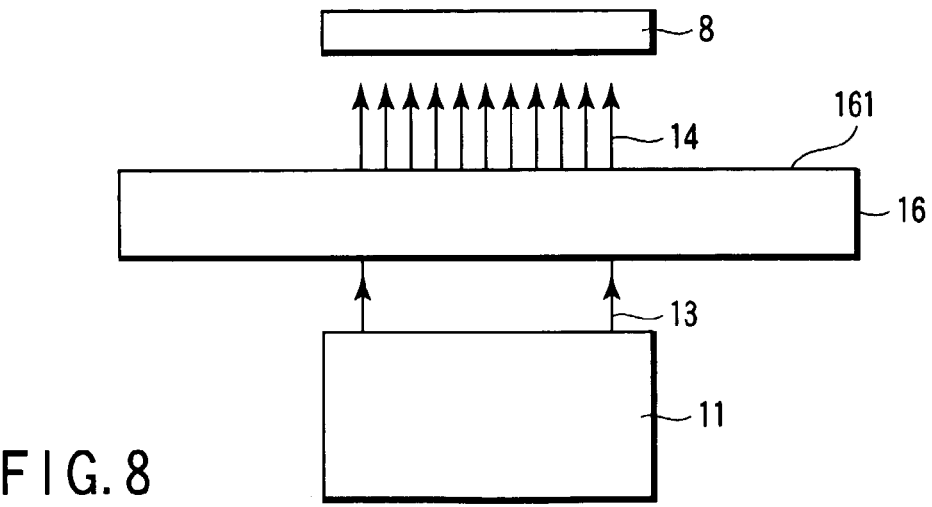
FIG. 8 is a conceptual diagram of the fluorescence film thickness measuring apparatus in a sixth embodiment of this invention.

FIG. 8 shows a sixth embodiment of this invention, and there are provided the ultraviolet light source 11 disposed under the organic EL device 16 and a two-dimensional sensor 8 typically used, such as a two-dimensional CCD sensor, disposed above the organic EL device 16. The ultraviolet light protection filter may be provided between the organic EL device 16 and the two-dimensional sensor 8 as needed. As the ultraviolet light source 11, a light source is used which is capable of releasing the ultraviolet light, such as the fluorescent test light, xenon lamp, deuterium lamp or nitrogen laser, having a wavelength to excite the organic materials constituting the organic EL device 16, preferably a wavelength of 200 nm to 380 nm.

For the two-dimensional CCD sensor 8, a digital still camera can be used, for example. Further, by placing these in the vacuum apparatus and measuring the fluorescence intensity of the organic thin film at the same time as the organic thin film formation, the film thickness can be controlled. To be specific, for example, the time-related change of the fluorescence intensity or the time-related change of the obtained film thickness is fed back to the power source of the deposition source and the shutter controller (not shown) to control the deposition rate, and further a film thickness control device (not shown) for terminating the film thickness formation at a target film thickness is provided, thereby enabling the film thickness control.

The organic thin film 161 is irradiated with the ultraviolet light 13 emitted from the ultraviolet light source 11. It is understood that the resolution within the surface during the film thickness distribution measurement is determined by the resolution of the two-dimensional CCD sensor 8 and measured area of each measured portion. The organic thin film 161 produces the fluorescence 14 having a wavelength inherent in the organic material by the irradiation of the ultraviolet light 13, and the two-dimensional CCD sensor 8, which is the photodetector, detects the fluorescence intensity of each portion. A two-dimensional distribution picture of the fluorescence intensity obtained from the two-dimensional CCD sensor 8 undergoes image processing, and is digitalized, whereby the film thickness distribution within the surface can be measured. Generally, an optical lens (not shown) for forming the fluorescence obtained from the two-dimensional CCD sensor 8 into an image is provided between the two-dimensional CCD sensor 8 and the organic thin film 161.

The sixth embodiment will further be described concretely. The mixture of polyvinylcarbazole and the coumarin dye is applied onto the glass substrate on which a film of indium tin oxide (ITO) is formed by the spray method from the dichloroethane solution in which polyvinylcarbazole and the coumarin dye are mixed. The thickness of the coating film by the spray method is supposedly thicker right under the spray and becomes thinner as the distance increases from the position right under the spray. ITO does not produce fluorescence by the irradiation of the ultraviolet light, and a green fluorescence derived from the coumarin dye is observed by irradiating the coating film of the mixture of polyvinylcarbazole and the coumarin dye with the ultraviolet light.

Figure 9:
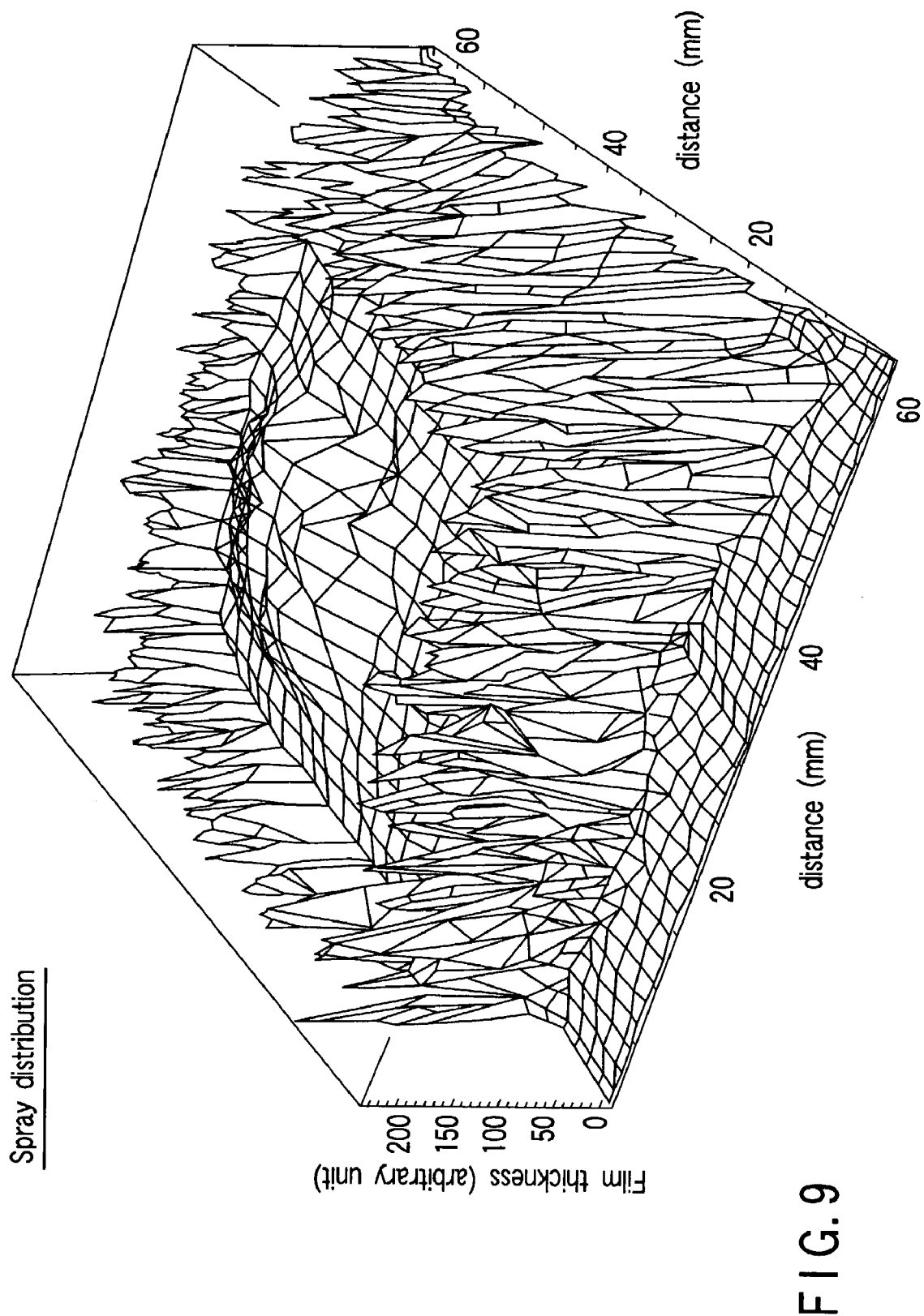
FIG. 9 is a diagram showing the measurement results of the in-surface distribution of film thickness according to the sixth embodiment.

The fluorescent test light (FI-3L manufactured by Toshiba Corporation) is placed as the light source 11 under the organic EL device 16, and a digital still camera (DSC-F55 manufactured by Sony Corporation) is placed as the photodetector 12 above the organic EL device 16. Image analysis is applied to a picture of the coating film showing the fluorescence picked up by the digital still camera, thus displaying the distribution of the fluorescence intensity in three dimensions. The in-surface distribution of the film thickness is measured from the fluorescence intensity. The measured film thickness in-surface distribution of the mixture of polyvinylcarbazole and the coumarin dye is shown in FIG. 9. The unit in a horizontal direction is nm, and the film thickness (vertical direction) is given an arbitrary scale. It is possible to control to obtain a predetermined thickness by measuring the relationship between application conditions such as viscosity, film formation temperature or the rate of the spray of the mixture, and the in-surface distribution of the formed film thickness. The same applies to the case of spin coating.

When the organic thin film is produced by deposition, the measurement system shown in FIG. 8 is placed in the vacuum apparatus 201, and the fluorescence intensity inherent in the organic thin film produced by the irradiation of the ultraviolet light during the deposition of the organic thin film is measured in parallel to and at the same time as the deposition process or at predetermined time intervals, thereby making it possible to control the film thickness. For example, the film thickness control portion 21 connected to the above digital still camera 12 and film thickness measurement portion 20 feeds the deposition conditions obtained in accordance with a predetermined algorithm of the CPU (not shown) in the film thickness control portion 21 on the basis of the measured fluorescence intensity distribution or the film thickness distribution calculated from this fluorescence intensity, back to the power source of the deposition source and/or the shutter controller (not shown)

capable of controlling the deposition amount, thereby allowing the deposition rate of the organic thin film and completion of the deposition at a target film thickness to be controlled.

According to the present invention, even when the organic EL device is constituted of a plurality of organic material layers of different components, by use of a plurality of band pass filters corresponding to the plurality of organic material layers, respectively, the thickness distribution of each organic layer can be measured. More specifically, the two-dimensional CCD sensor 8 or the like sequentially measures each fluorescence having passed through the filter that would allow only fluorescence peak wavelengths from the organic layers to be measured to pass, among a plurality of fluorescence spectrum wavelengths having a wavelength inherent in each material produced at the same time from the organic materials constituting the respective organic layers, so that the thickness distribution of each organic layer can be measured from the intensity distribution of the peak wavelengths of each fluorescence.

Some embodiments of the present invention have been illustrated in the drawings and described above, but the embodiments of the present invention described herein are given as mere examples, and it is apparent that various modifications may be made without departing from the technical scope of the present invention. To facilitate the description of the present invention, it has only been described that the light source capable of emitting an ultraviolet light is used as the light source for fluorescent excitation, but it is possible to use a light source having a longer wavelength or a light source having a shorter wavelength when necessary.

As has been described above, measuring the fluorescence intensity of the organic thin film for use in the organic EL device according to the present invention facilitates the more accurate and simpler measurement of the thickness distribution within the surface of the organic thin film. It is also possible to successively measure each layer at the same time with respect to the organic thin film having a plurality of thin layers made of different materials.

Furthermore, it is possible to readily control the growth rate of the organic thin film during an organic thin film producing step and control the film thickness.

What is claimed is:

1. A method for irradiating an organic thin film for use in an organic electroluminescence device with an ultraviolet light to measure a relative thickness distribution of the organic thin film, the method comprising:
   irradiating a predetermined region of the organic thin film formed on a transparent substrate with the ultraviolet light through a pin hole disposed between an ultraviolet light source and the transparent substrate;
   measuring the intensity of a fluorescence produced by the organic thin film in response to the light irradiation from a permeation emitting side of the ultraviolet light through a filter shutting off the irradiated ultraviolet light;
   obtaining a film thickness of the predetermined region of the organic thin film from the intensity of the fluorescence; and
   obtaining the film thickness distribution of the organic thin film from the film thickness of each region of the organic thin film.

2. The measuring method according to claim 1, comprising:
   placing the organic thin film on an XY movable stage; and
   scanning light irradiated positions in the organic thin film by the XY movable stage.

3. The measuring method according to claim 1, wherein the filter is a long wavelength pass light filter.

4. The measuring method according to claim 1, wherein the filter is a band pass light filter.

5. A method for forming an organic thin film on a transparent substrate by a vacuum deposition method, comprising:
   measuring a film thickness by use of a measuring method according to any one of claims 1 to 4 to control the thickness of the organic thin film.

6. A method for forming an organic thin film on a transparent substrate by a spin coat method, comprising:
   measuring a film thickness by use of a measuring method according to any one of claims 1 to 4 to control the thickness of the organic thin film.

7. A method for forming an organic thin film on a transparent substrate by a spray coat method, comprising:
   measuring a film thickness by use of a measuring method according to any one of claims 1 to 4 to control the thickness of the organic thin film.

8. An apparatus for irradiating an organic thin film for use in an organic electroluminescence device with an ultraviolet light to measure a relative thickness distribution of the organic thin film, the apparatus comprising:
   means for irradiating a predetermined region of the organic thin film formed on a transparent substrate with a light including an ultraviolet light;
   pin hole forming means disposed between an ultraviolet light source and a transparent substrate;
   means for measuring from a permeation emitting side of the ultraviolet light the intensity of a fluorescence produced by the organic thin film,
   wherein a filter for shutting off the irradiated ultraviolet light is provided between the organic film and the measuring means; and
   means for obtaining the film thickness of the predetermined region from the intensity of the fluorescence,
   wherein the film thickness distribution of the organic thin film is obtained from the film thickness of each region of the organic thin film.

9. The measuring apparatus according to claim 8, further comprising an XY movable stage which mounts the organic thin film formed on a transparent substrate thereon and which can scan light irradiated positions in the organic thin film.

10. The measuring apparatus according to claim 8, wherein the filter is a long wavelength pass light filter.

11. The measuring apparatus according to claim 8, wherein the filter is a band pass light filter.

12. An apparatus for forming an organic thin film on a transparent substrate by a vacuum deposition method, wherein a film thickness is controlled by a film thickness control device for the organic thin film connected to a measuring apparatus according to any one of claims 8 to 11.

13. An apparatus for forming an organic thin film on a transparent substrate by a spin coat method, wherein a film thickness is controlled by a film thickness control device for the organic thin film connected to a measuring apparatus according to any one of claims 8 to 11.

14. An apparatus for forming an organic thin film on a transparent substrate by a spray coat method, wherein a film thickness is controlled by a film thickness control device for the organic thin film connected to a measuring apparatus according to any one of claims 8 to 11.

15. A fluorescence intensity measuring apparatus for irradiating an organic thin film with an ultraviolet light to measure a relative fluorescence intensity thereof when forming a thin organic film for use in an organic electroluminescence device, the apparatus comprising:
- means for irradiating a predetermined region of the organic thin film formed on a transparent substrate with the ultraviolet light;
- pin hole forming means disposed between an ultraviolet light source and a transparent substrate; and
- means for measuring from a permeation emitting side of the ultraviolet light the intensity of fluorescence produced by the organic film;
- wherein a filter for shutting off the irradiated ultraviolet light is provided between the organic film and the measuring means, and
- the fluorescence intensity corresponding to an electroluminescence intensity of the organic electroluminescence device formed in the predetermined region is measured.

16. The apparatus according to claim 15, further comprising an XY movable stage which mounts the organic thin film formed on a transparent substrate thereon and which can scan light irradiated positions in the organic thin film.

17. The apparatus according to claim 15, wherein the filter is a long wavelength pass light filter.

18. The apparatus according to claim 15, wherein the filter is a band pass light filter.

19. A method for forming an organic thin film on a transparent substrate by a vacuum deposition method, wherein a fluorescence intensity is measured and a supply amount of an organic thin film material is controlled using the measuring apparatus of any one of claims 15–18.

20. An apparatus for forming an organic thin film on a transparent substrate by a spin coat method, wherein a fluorescence intensity is measured and a supply amount of an organic thin film material is controlled using the measuring apparatus of any one of claims 15–18.

21. An apparatus for forming an organic thin film on a transparent substrate by a spray coat-method, wherein a fluorescence intensity is measured and a supply amount of an organic thin film material is controlled using the measuring apparatus of any one of claims 15–18.

* * * * *